US012727836B2

(12) United States Patent
Lauer et al.

(10) Patent No.: US 12,727,836 B2
(45) Date of Patent: Sep. 8, 2026

(54) HYGIENE COVER FOR A MEDICAL IMAGING DEVICE

(71) Applicants: Siemens Healthineers AG, Forchheim (DE); Dentsply Sirona Inc., York, PA (US); SIRONA Dental Systems GmbH, Bensheim (DE)

(72) Inventors: Lars Lauer, Neunkirchen (DE); Andreas Greiser, Erlangen (DE); Stephan Biber, Erlangen (DE); Gunnar Krüger, Binningen (CH); Daniel Rinck, Forchheim (DE); Carmel Hayes, Munich (DE); Kim Burzan, Birkenau (DE); Johannes Ulrici, Darmstadt (DE)

(73) Assignees: Siemens Healthineers AG, Erlangen (DE); Dentsply Sirona Inc., York, PA (US); SIRONA Dental Systems GmbH, Bensheim (DE)

( * ) Notice: Subject to any disclaimer, the term of this patent is extended or adjusted under 35 U.S.C. 154(b) by 266 days.

(21) Appl. No.: 18/520,288

(22) Filed: Nov. 27, 2023

(65) Prior Publication Data

US 2024/0206834 A1 Jun. 27, 2024

(30) Foreign Application Priority Data

Dec. 23, 2022 (EP) .................................... 22216502

(51) Int. Cl.

| | |
|---|---|
| ***A61B 6/00*** | (2024.01) |
| ***A61B 46/10*** | (2016.01) |
| *A61B 46/20* | (2016.01) |

(52) U.S. Cl.

CPC ............ *A61B 6/4423* (2013.01); *A61B 46/10* (2016.02); *A61B 2046/205* (2016.02); *A61B 2562/247* (2013.01)

(58) Field of Classification Search

CPC ........ A61B 2046/205; A61B 2562/247; A61B 46/10; A61B 5/055; A61B 6/035; A61B 6/037; A61B 6/4423; A61B 6/502; A61N 2005/1097; A61N 5/1049

See application file for complete search history.

(56) References Cited

U.S. PATENT DOCUMENTS

| | | | |
|---|---|---|---|
| 6,105,579 A | 8/2000 | Levitt et al. | |
| 11,246,674 B1 * | 2/2022 | Galbierz ................ | A61G 10/02 |
| 2010/0004529 A1 | 1/2010 | Henke-Sarmento | |
| 2014/0275973 A1 | 9/2014 | Schuele | |
| 2015/0011870 A1 | 1/2015 | Piferi | |

(Continued)

FOREIGN PATENT DOCUMENTS

| | | |
|---|---|---|
| DE | 102017205412 A1 | 10/2018 |
| DE | 102021202912 A1 | 4/2022 |

(Continued)

*Primary Examiner* — Mark D Remaly

(74) *Attorney, Agent, or Firm* — Banner & Witcoff, Ltd.

(57) ABSTRACT

The disclosure relates to a hygiene cover for preventing a contamination of a target surface of a medical imaging device. The hygiene cover is configured for reversibly attaching to the target surface of the medical imaging device and/or a body region of a patient, and the reversible attachment is configured to provide for maintaining a predefined relative position of the hygiene cover to the medical imaging device.

20 Claims, 7 Drawing Sheets

(56) References Cited

U.S. PATENT DOCUMENTS

| | | | |
|---|---|---|---|
| 2016/0131724 | A1 | 5/2016 | Balaban et al. |
| 2016/0135896 | A1 | 5/2016 | Fink |
| 2017/0273751 | A1 | 9/2017 | Czajka et al. |
| 2021/0045829 | A1 | 2/2021 | Bishop |
| 2021/0401529 | A1 | 12/2021 | Daley, II et al. |

FOREIGN PATENT DOCUMENTS

| | | | |
|---|---|---|---|
| EP | 3461408 | A1 | 4/2019 |
| WO | 2014205275 | A1 | 12/2014 |

* cited by examiner 11
16a
30
12
12
30
16b
50
43
12

HYGIENE COVER FOR A MEDICAL IMAGING DEVICE

CROSS-REFERENCE TO RELATED APPLICATIONS

The present application claims priority to and the benefit of European patent application no. EP 22216502.9, filed on Dec. 23, 2022, the contents of which are incorporated herein by reference in their entirety.

TECHNICAL FIELD

The disclosure relates to a hygiene cover for a medical imaging device.

BACKGROUND

Medical imaging devices are widely used for generating diagnostic image data of patients. When imaging a patient, particularly a head region of a patient, parts of the medical imaging device may be positioned close to the patient or even get into direct contact with the patient's skin. For example, means for fixing and/or supporting body regions of the patient during an imaging examination bear a particularly high risk of being exposed to contaminants, such as saliva or other bodily fluids. However, contamination may also pose a problem in narrow spaces within an imaging region of the medical imaging device as well as on imaging components positioned in proximity to the patient, such as emitters and/or detectors in x-ray devices, radio-frequency coils in magnetic resonance devices, cameras for volume photography, and the like.

Medical imaging devices which generate images from a head region of the patient are particularly prone to contamination. In order to avoid any irritation of the patient or interference with the patient's breathing, covering the patient's skin may not an option. The problem of contamination becomes even more prominent in imaging devices, which are directed at generating images from a jaw region, particularly the teeth, of the patient. In case of magnetic resonance devices, dedicated receive coils need to be positioned close to a jaw area around the patient's mouth and nose. These dedicated receive coils are not only subject to significant contamination by breathing, spitting, and/or sneezing, but also to contamination by direct skin contact, for example with the patient's cheeks. The use of makeup or crème can also be problematic in contamination of surfaces of the medical imaging devices.

SUMMARY

Conventionally, the above-mentioned problems have been addressed by wiping respective parts of the medical imaging devices with disinfectants and/or solvents.

It is an objective of the disclosure to improve and/or facilitate an imaging examination of a patient. This objective is achieved by a hygiene cover and a medical imaging device according to the embodiments of the disclosure as further described herein, including the claims.

The hygiene cover is configured for preventing a contamination of a target surface of a medical imaging device.

A medical imaging device may be any suitable device configured to generate diagnostic images from an exterior and/or an interior of a patient. Examples for medical imaging devices magnetic resonance devices, x-ray devices, computed tomography devices, mammography devices, positron emission tomography devices, single-photon emission computed tomography devices, high resolution cameras, etc. For example, the medical imaging device may be configured to perform an imaging examination of the patient to acquire (diagnostic) image data of a body region of the patient.

A target surface of the medical imaging device may represent any surface of the medical imaging device and/or of a peripheral component of the medical imaging device. For example, the target surface may relate to a surface of a radio-frequency coil of a magnetic resonance device, a surface of an emitter and/or detector of an x-ray device, or a surface of a camera. For example, the target surface may relate to a surface of a supporting structure (i. e. a patient support) configured for supporting and/or fixing the body region of the patient in a predefined relative position to the medical imaging device.

In one embodiment, the target surface relates to a surface of the medical imaging device facing in a direction of the body region of the patient when the patient is positioned in an appropriate position for performing an imaging examination with the medical imaging device.

The hygiene cover may be configured to cover the target surface to prevent a deposition of contaminants on the target surface. For example, the hygiene cover may comprise or consist of one or more layers or materials configured for preventing a transport of contaminants through or over the hygiene cover in the direction of the target surface.

The term "contaminant" may relate to any kind of bacterium, virus, spore, dirt, debris, particle, fluid, and/or bodily fluid undesirable on the target surface.

The hygiene cover is configured for reversibly (i.e. removably in that the attachment may be reversed) attaching to the target surface of the medical imaging device. For example, the hygiene cover may also be configured for reversibly attaching to a body region of a patient.

The term patient comprises human patients and animal patients.

The hygiene cover may comprise a body shaped in conformity with a shape of the target surface. However, the body of the hygiene cover may also be shaped in conformity with a body region of a patient. The body of the hygiene cover may be rigid or flexible. For example, the body of the hygiene cover may be formed as a sheet, a cloth, a foam padding, a block, etc. The body of the hygiene cover may comprise a substantially two-dimensional or a three-dimensional shape. It is conceivable that the body of the hygiene cover comprises or consists of several sections, layers, and/or materials having different structural and/or functional properties.

In an embodiment, the body of the hygiene cover is malleable to allow for a modification of the shape of the hygiene cover to match the shape of the target surface and/or the body region of the patient.

In an embodiment, the hygiene over comprises one or more materials configured to withstand autoclave temperatures, thus allowing for autoclaving and reusing the hygiene cover.

According to a further embodiment, the hygiene cover comprises one or more materials that can be reprocessed close to 100%, such as polymers or cellulose material.

In providing a hygiene cover made of the above-mentioned materials, a sustainability of the hygiene cover may favorably be increased.

In one embodiment, at least a section of the hygiene cover comprises glass. Glass is a favorable material due to its high scratch resistance, transparency, high structural rigidity, high resistance against solvents, and/or easy-to-clean (non-porous) surface. In an embodiment, the hygiene cover comprises glass.

In a further embodiment, the hygiene cover is configured for providing mechanical support to a peripheral component of the medical imaging device comprising the target surface. For example, the hygiene cover may provide a fixture configured to carry a local coil and/or an antenna of a local coil. It is conceivable that the hygiene cover is configured for maintaining a relative position of the local coil to the medical imaging device throughout an imaging examination. For example, the hygiene cover may provide a protective and/or anti-contaminative function as well as a supporting function, thus favorably enhancing compactness and/or functional density of the medical imaging device.

The hygiene cover is configured for reversibly attaching (again, removably attaching) to the target surface of the medical imaging device, but also to the body region of the patient. For example, the hygiene cover allows for a residue-free removal of the hygiene cover from the target surface and/or the body region of the patient. It is also conceivable that the hygiene cover is a disposable item configured for a single use. For example, the hygiene cover may comprise a fastening element configured to provide a detachable mechanical connection with the target surface and/or the body region of the patient.

According to the disclosure, the reversible (i.e. removable) attachment is configured for maintaining a predefined relative position of the hygiene cover to the medical imaging device.

For example, the reversible attachment is configured for maintaining the predefined relative position of the hygiene cover to the medical imaging device. For example, the hygiene cover may be reversibly attached to the medical imaging device and optionally the target surface, in the predefined relative position to the medical imaging device. However, it is conceivable that the hygiene cover is reversibly attached to the body region of the patient. In this case, maintaining the predefined relative position of the hygiene cover to the medical imaging device may be assisted or accomplished via a support structure supporting the patient in maintaining a predefined relative position to the medical imaging device.

The predefined relative position of the hygiene cover to the medical imaging device may be characterized by a covering or screening of at least a section of the target surface via the hygiene cover. However, the predefined relative position of the hygiene cover to the medical imaging device may also be characterized by a covering or screening of at least a section of the body region of the patient via the hygiene cover. It is also conceivable that the predefined relative position of the hygiene cover to the medical imaging device is characterized by a direct contact between the hygiene cover and the target surface, but also the body region of the patient. For example, the hygiene cover may be configured for directly attaching to the target surface and the body region of the patient. According to an embodiment, the predefined relative position of the hygiene cover to the medical imaging device is characterized by a predefined position and a predefined orientation of the hygiene cover with respect to the medical imaging device. It is also conceivable that the hygiene cover is reversibly attached to the body region of patient, while the body region is fixed in a predefined relative position to the medical imaging device via a suitable support structure. Thus, the hygiene cover may be positioned in the relative position to the medical imaging device while being reversibly attached to the body region of the patient.

The reversible attachment may be configured for maintaining the predefined relative position of the hygiene cover to the medical imaging device, e.g. the target surface, throughout an imaging examination. For example, the reversible attachment is configured to withstand a movement of the patient and/or a predefined maximum force exerted by the patient onto the hygiene cover. Thus, an unintentional detaching of the hygiene cover from the target surface and/or the body region of the patient and/or an unintentional departing of the hygiene cover from the predefined relative position to the medical imaging device may be avoided.

In an embodiment, the reversible attachment allows for a manual detachment or removal of the hygiene cover from the target surface and/or the body region of the patient. For example, the hygiene cover may be removed from the target surface and/or the body region of the patient by an operator of the medical imaging device and/or the patient.

In one embodiment, a section or layer of the hygiene cover may comprise a surface charge opposite to a surface charge of the target surface. Thus, the reversible attachment of the hygiene cover to the target surface may be provided via an electrostatic force or electrostatic attraction. In providing an electrostatically pre-charged hygiene cover, an additional fastening element configured for reversibly attaching the hygiene cover to the target surface and/or the body region of the patient may favorably be omitted.

In a further embodiment, the reversible attachment is configured to require a dedicated instrument or tool for detaching the hygiene cover from the target surface and/or the body region of the patient.

In still a further embodiment, the reversible attachment is configured to require a dedicated deactivation process for detaching the hygiene cover from the target surface and/or the body region of the patient.

For example, the reversible attachment may be configured to require a dedicated activation process for reversibly attaching the hygiene cover to the target surface and/or the body region of the patient.

The hygiene cover may comprise a biocompatible material. A biocompatible material may be characterized by a lack of undesirable side effects on a living object, such as a patient. For example, a biocompatible material may be histopathologically harmless, non-toxic, and/or exhibit a high cell and blood tolerance.

In one embodiment, the hygiene cover may comprise or consist of a plastic material, such as polyethene, polyamide, polyester polycarbonate, polyurethane, polymethyl methacrylate (acrylic glass), or a similar polymer. However, other materials are also conceivable. The hygiene cover may comprise homogeneous sections, but also sections comprising material layers and/or a functional coating. When the hygiene cover is positioned in the predefined relative position to the medical imaging device, at least one surface or side of the hygiene cover facing in a direction of the patient may comprise a natural material, such as cotton, plant fiber, wool, hemp, etc. Thus, a comfort of the patient may favorably be increased and/or requirements regarding biocompatibility may favorably be met.

The hygiene cover favorably allows for a time-efficient installation of the hygiene cover in the predefined relative position to the medical imaging device. For example, the hygiene cover may favorably accelerate a workflow related to a preparation and/or performance of an imaging examination of the patient with the medical imaging device.

As a further advantage, the hygiene cover may reduce or eliminate a requirement of disinfecting the target surface of the medical imaging device, thus reducing costs and/or a workload of personnel regarding the preparation of the imaging examination.

According to an embodiment, the hygiene cover comprises a fastening element, wherein the reversible attachment of the hygiene cover to the target surface and/or the body region of the patient is provided via the fastening element. The fastening element is configured for providing a mechanical connection between the hygiene cover and the medical imaging device and/or between the hygiene cover and the patient.

A mechanical connection may comprise a form-locking connection and/or a force-locking connection. It is also conceivable that the mechanical connection comprises a material connection, such as an adhesive bond.

For example, the fastening element and/or the target surface may comprise a hook-and-loop, a hook-and-pile, or a touch fastening mechanism. The fastening mechanism may comprise a first fabric element attached to the target surface and a second fabric element attached to a surface of the hygiene cover to be reversibly attached to the target surface. The first fabric element may comprise hooks, whereas the second fabric element may comprise loops (or vice-versa). The hooks may be configured to catch in the loops when the hygiene cover is positioned in the predefined relative position to the medical imaging device and provide the reversible attachment. The fastening element may comprise the first fabric element and/or the second fabric element.

In a further example, the fastening element may comprise a securing pin, a plug connector, a buckle connector, a latching mechanism, a clamping mechanism, etc. The fastening may be configured to provide a form-locking and/or force locking connection between the hygiene cover and the target surface and/or the body region of the patient.

According to an embodiment, the fastening element comprises an adhesive layer configured to provide a reversible adhesive bond between the target surface and the hygiene cover. For example, the adhesive layer may be positioned on a surface of the hygiene cover to be reversibly attached to the target surface. However, the adhesive layer may also be positioned on the target surface. It is conceivable that at least a section of the hygiene cover and/or the target surface is devoid of the adhesive layer to facilitate a process of detaching the hygiene cover from the target surface.

In providing a hygiene cover with an fastening element, detaching the hygiene cover from the target surface and/or the body region of the patient may favorably be carried out in a non-destructive manner. Thus, the hygiene cover may be reused after cleaning and/or disinfecting the hygiene cover in a dedicated process.

Furthermore, the fastening element may favorably provide for a profound mechanical connection between the hygiene cover and the target surface and/or the body region of the patient. Thus, any deviation of a position of the hygiene cover from the predefined relative position during an imaging examination may favorably be prevented.

In a further embodiment, the hygiene cover comprises an adhesive layer configured for providing a reversible adhesive bond between the hygiene cover and the target surface. The adhesive layer is configured in such a way to enable the reversible adhesive bond to be activated and/or deactivated via a dedicated activation and/or deactivation process, respectively.

The adhesive layer may be located on a surface of the hygiene cover and/or the target surface.

The dedicated activation and/or deactivation process may be characterized by a physical interaction with the adhesive layer. For example, the dedicated activation and/or deactivation process may involve mechanically deforming and/or heating the adhesive layer and/or removing a protective layer from the adhesive layer.

In an embodiment, the hygiene cover comprises a protective layer or film covering a section of the adhesive layer to be reversibly attached to the target surface. The activation process may comprise detaching the protective layer or film from the adhesive layer. The protective layer may favorably prevent the adhesive layer from resorbing dirt and/or contaminants before the hygiene cover is reversibly attached to the target surface.

In one embodiment, an adhesive property of the adhesive layer may be heat-sensitive. For example, the activation process may comprise heating the adhesive layer. In providing heat, the adhesive layer may be thermally activated, thus developing and/or improving an adhesive property and/or facilitating a process of positioning the hygiene cover in the predefined relative position.

In an embodiment, the deactivation process comprises heating the hygiene cover to decrease an adhesive property of the adhesive layer. Thus, an effort required for detaching the hygiene cover from the target surface may favorably be decreased. The adhesive layer may be heat-sensitive in any suitable temperature range, e.g. between 10 and 70 degrees Celsius, between 15 and 50 degrees Celsius, between 20 and 40 degrees Celsius, etc.

In a further embodiment, a surface of the hygiene cover comprises a perforation connectable to a vacuum system. The surface comprising the perforation is configured to reversibly attach to the target surface via a negative pressure provided by the vacuum system.

The surface comprising the perforation may form a part of a fastening element as specified above. For example, the surface comprising the perforation may represent the fastening element.

The surface of the hygiene cover may comprise one or more perforations. A perforation may be a hole or an opening with an arbitrary shape. For example, the surface to be reversibly attached to the target surface may comprise a plurality of perforations distributed in regular or irregular intervals. In providing a plurality of perforations, folds, and/or wrinkles in the hygiene cover may favorably be avoided when the hygiene cover is reversibly attached to the target surface. For example, the hygiene cover may be implemented as a bag or tube encompassing a section of the medical imaging system, such as a local coil, comprising the target surface. The hygiene cover may be sucked flat to the target surface by removing all included air via the vacuum system, thus providing a tight and fold-free enclosure for the local coil with minimum user interaction.

The hygiene cover may comprise at least a part of the vacuum system. For example, the hygiene cover may comprise a piping system or channels connecting the perforation to the vacuum system. The piping system or channels may be embedded within the hygiene cover. The hygiene cover may also comprise a (quick) connector configured for connecting the piping system or the channels to the vacuum system. For example, the one or more perforations do not extend through the body of the hygiene cover but connect to channels or a piping system embedded within the hygiene cover.

The vacuum system may be driven by a compressor, a fan, a vacuum pump, or the like. The vacuum system may provide a negative pressure at inlets of the one or more perforations. Thus, when positioning the hygiene cover in the predefined relative position to the medical imaging device, the hygiene cover may reversibly attach to the target surface via the negative pressure applied to the one or more perforations.

A hygiene cover connectable to a vacuum system may provide a particularly time-efficient and/or easy-to-use means for providing a reversible attachment between the hygiene cover and the target surface.

In an embodiment, at least a section of the hygiene cover comprises a flexible material and/or a flexible element configured to be modified in such a way that a shape of the hygiene cover conforms to a shape of the target surface of the medical imaging device and/or the body region of the patient.

The flexible element may allow for a folding of one or more sections of the hygiene cover. For example, the flexible element may comprise a hinge or a moveable joint. Thus, the hygiene cover may be folded to a shape or contour of the target surface and/or the body region of the patient.

For example, the hygiene cover may comprise or consist of a flexible material. The flexible material may be malleable. For example, the flexible material may be configured be deformed with manual effort. For example, the flexible material may be configured to allow for deforming the hygiene cover in such a way that a shape or contour of the hygiene cover corresponds to a shape or contour of the target surface and/or the body region of the patient. Suitable flexible materials include plastics such as polyethene, polyurethane, polyamide, and polyester. The flexible material may be plastically or elastically deformable.

In one embodiment, the flexible material is a foam. A foam may have a low density and thus a low weight. In addition to the materials mentioned above, the flexible material may also be based on a natural material, such as wool, plant fibers, leather, etc.

The hygiene cover may favorably be formed or modified to adapt to shapes or contours of body regions of different patients. Thus, the hygiene cover may allow for a precise fit on different patients and/or different medical imaging devices, even when provided in a standardized size.

According to a further embodiment, the hygiene cover is formed as a bag or tube comprising at least one opening configured for circumferentially encompassing a section of the medical imaging device comprising the target surface or the body region of the patient.

The hygiene cover may be configured for accommodating the target surface or the body region of the patient within the at least one opening. It is also conceivable that the hygiene cover is configured for accommodating a section or part of the medical imaging device within the at least one opening.

For example, the hygiene cover may comprise an elastic material. The elastic material may favorably allow for stretching of the hygiene cover and/or adapting a size of the at least one opening to fit different patients and/or facilitate a process of attaching the hygiene cover to the target surface and/or the body region of the patient.

The section of the medical imaging device may be a patient support structure, such as a chin rest, a mouthpiece, a jaw support, a neck support, a section of a patient bore or gantry, etc. However, the section of the medical imaging device may also relate to a section of an imaging component of the medical imaging device, such as a body coil, a radiofrequency coil, a camera, and/or an emitter/detector unit.

In one embodiment, the hygiene cover is formed as a bag configured for accommodating the section of the medical imaging device comprising the target surface within an interior volume of the bag. For example, a shape of the bag corresponds to a shape of the part of the medical imaging device. The bag may comprise a fastening element according to an embodiment described above. For example, the fastening element may be configured for tightening a rim forming the opening of the bag onto the section of the medical imaging device.

The hygiene cover may also be formed as a tube, such as a loop or a hollow cylinder. The hygiene cover may have an appropriate size to fit the section of the medical imaging device comprising the at least one surface and/or the body region of the patient.

The hygiene cover may also take the form of a substantially planar sheet. For example, the hygiene cover may comprise a fastening mechanism including a first fabric element and a second fabric element according to an embodiment described above. The first fabric element and the second fabric element may be positioned at two opposing ends or sides of the hygiene cover. Thus, the hygiene cover may be formed around the section of the medical imaging device and/or the body region of the patient and reversibly attach to the target surface and/or the body region of the patient by connecting the first fabric element to the second fabric element. By connecting the first fabric element to the second fabric element, the hygiene cover may form a loop encompassing the target surface and/or the body region of the patient.

A bag-shaped or tube-shaped hygiene cover may favorably facilitate a process of attaching the hygiene cover to the target surface of the medical imaging device and/or the body region of the patient. Furthermore, in providing a hygiene cover made of an elastic material, the hygiene cover may favorably conform to more complex surface contours or shapes of the target surface and/or the body region of the patient. Thus, any crevices or gaps between the hygiene cover and the target surface and/or body region of the patient may be prevented. As a further advantage, a risk of slipping or shifting of the hygiene cover during an imaging examination may be reduced due to contracting forces of the elastic material.

In a further embodiment, the hygiene cover comprises a perforation shaped in correspondence with an opening in the target surface of the medical imaging device. The hygiene cover is shaped in such a way to allow for the perforation to be positioned congruently with the opening in the target surface when the hygiene cover is positioned in the predefined relative position to the medical imaging device.

An opening in the target surface may have a functional and/or a structural purpose. For example, the opening in the target surface may relate to a hole in a radiofrequency-coil positioned directly on or in proximity to the body region of the patient. The opening may be configured to allow for medical instruments and/or a support structure to pass through the opening. However, the opening in the target surface may also provide a viewing window and/or an opening for breathing, particularly if the head of the patient is positioned close to the target surface. The opening in the hygiene cover may be provided, for example, via a punching process.

The hygiene cover may comprise one or more perforations positioned congruently with one or more openings in the target surface when the hygiene cover is positioned in the predefined relative position to the medical imaging device.

In providing a hygiene cover with one or more perforations, an obstruction of a sight and/or breathing of the patient may favorably be prevented. Furthermore, a perforation may favorably allow for medical instruments and/or a support structure to extend through the hygiene cover while reducing a risk of contamination of the target surface.

In an embodiment, the hygiene cover is embodied as a mask shaped in conformity with a part of a facial region of the patient.

For example, the hygiene cover may be formed as a tube or a band comprising an opening configured for accommodating head region of the patient as described above. For example, the hygiene cover comprises an elastic material configured for reversibly attaching the hygiene cover to the head of the patient via elastic contraction. Thus, the elastic material of the hygiene cover may act as a fastening element.

In one embodiment, the hygiene cover is made of a flexible material and comprises a substantially planar shape. The hygiene cover may comprise a fastening element according to an embodiment described above. For example, the hygiene cover may comprise a fastening element, such as a hook-and-loop fastening mechanism. Thus, the hygiene cover may be formed around and reversibly attached the body region, e.g. a head region, of the patient.

In an embodiment, the hygiene cover comprises a perforation shaped in correspondence with a facial feature of the patient. The hygiene cover is shaped in such a way to allow for the perforation to be positioned congruently with the facial feature of the patient when the hygiene cover is positioned in the predefined relative position to the medical imaging device.

For example, the facial feature of the patient may relate to the nose, the mouth, an ear, and/or an eye of the patient.

The hygiene cover may comprise one or more perforations positioned congruently with one or more facial features of the patient when the hygiene cover is positioned in the predefined relative position to the medical imaging device. For example, the one or more perforations may provide a viewing window and/or an opening for breathing. However, as described above, the one or more perforations may also provide an access of a medical instrument to the body region, e.g. the facial feature, of the patient.

In providing an hygiene cover, a risk of contamination of the target surface of the medical imaging device may favorably be reduced with minimal impairment of the patient and/or restriction of access to the patient.

In an alternative embodiment, the hygiene cover may comprise a section made of a transparent material. The section made of the transparent material may be positioned congruently with an eye of the patient when the hygiene cover is positioned in the predefined relative position to the medical imaging device.

According to a further embodiment, the hygiene cover comprises a barrier layer configured for preventing a transport of a substance from the patient onto the target surface through and/or via the hygiene cover.

In one embodiment, the barrier layer comprises a material configured for slowing down or preventing diffusion and/or capillary transport of substances from the patient, e.g. from the skin of the patient, through the barrier layer.

The barrier layer may comprise one or more layers. A first layer of the barrier layer may be configured to slow down or prevent diffusion of water-soluble or hydrophilic substances through the first layer. Likewise, a second layer may be configured to slow down or prevent diffusion of organic or lipophilic substances through the second layer. Of course, the barrier layer may comprise other and/or additional layers configured for slowing down diffusion and/or preventing diffusion of substances typically found on the skin of a patient.

For example, the barrier layer may be configured to slow down or prevent vaporous bodily fluids from passing through the barrier layer. For example, the barrier layer may comprise a porous structure with a high surface area and/or an adsorbent configured to adsorb vaporous body fluids.

The barrier layer may comprise or consist of one or more materials. For example, the barrier layer may comprise glass, which provides an adequate barrier against molecular diffusion. However, some of the polymers described above (i. e. polycarbonate or polymethyl methacrylate) may also provide an adequate material for the barrier layer.

In providing an hygiene cover comprising a barrier layer, a risk of contamination of the target surface may favorably be reduced or minimized.

In one embodiment of the hygiene cover, at least a section of the hygiene cover is shaped in such a way to fill a gap between the target surface of the medical imaging device and the body region of the patient when the hygiene cover is positioned in the predefined relative position to the medical imaging device and the patient.

For example, a side of the hygiene cover facing in a direction of the target surface may be shaped in correspondence with a shape or contour of the target surface when the hygiene cover is attached to the body region of the patient and/or the target surface in the predefined relative position to the medical imaging device. Likewise, a side of the hygiene cover facing in a direction of the body region of the patient may be shaped in correspondence with a shape or contour of the body region of the patient when the hygiene cover is attached to the body region of the patient and/or the target surface in the predefined relative position. In one embodiment, the side of the hygiene cover facing in the direction of the target surface may comprise a different shape in comparison to the side of the hygiene cover facing in the direction of the body region of the patient.

For example, the hygiene cover may have any suitable thickness such as e.g. more than 1 mm, 2 mm, 3 mm, 4 mm, more than 5 mm, etc. The thickness of the hygiene cover may also exceed for example 10 mm, 20 mm, 30 mm, 40 mm, 50 mm, etc. The gap or space between the target surface and the body region of the patient may be fully occupied by the hygiene cover. Thus, the patient may favorably be positioned at a predefined distance to the target surface while a contact between the target surface, the hygiene cover and the body region of the patient may be maintained.

In one embodiment, the hygiene cover comprises or consists of an elastic material, such as an elastic foam. The elastic material may allow for a compression or deformation of the hygiene cover. For example, the elastic material may allow for an adaption of the shape of the hygiene cover to conform to the shape or contour of the target surface and/or the body region of the patient. Thus, the hygiene cover may favorably provide support to the patient and/or prevent movement of the body region of the patient relative to the target surface.

In an alternative embodiment, the hygiene cover comprises a non-elastic material. In this case, the side of the hygiene cover facing in the direction of the target surface may be shaped or molded in correspondence with the shape of the target surface. Likewise, the side of the hygiene cover facing in the direction of the body region of the patient may be shaped or molded in correspondence with a surface of the body region of the patient.

The hygiene cover may favorably prescribe a distance between the target surface and the body region of the patient. Thus, the hygiene cover may favorably facilitate a process of positioning the patient in a predefined relative position to the medical imaging device.

According to a further embodiment, the hygiene cover comprises at least one marker. The at least one marker is configured to provide guidance for aligning the at least one marker with at least one landmark on the target surface of the medical imaging device when reversibly attaching the hygiene cover to the target surface in the predefined relative position to the medical imaging device.

The at least one marker may comprise a structural feature, such as a pin, a recess, a groove, a notch, a bolt, a screw, etc. However, the at least one marker may also comprise a visual feature, such as an arrow, a picture, a pictogram, a symbol, a geometric pattern, etc.

For example, the at least one marker may be positioned on a surface of the hygiene cover to be attached to the target surface.

In one embodiment, the at least one marker is positioned congruently to at least one landmark on the target surface when the hygiene cover is attached to the target surface and/or the body region of the patient in the predefined relative position to the medical imaging device.

For example, the at least one marker may comprise a structural feature and the at least one landmark on the target surface comprises a structural feature complementary to the at least one marker. It is conceivable that the structural feature on the target surface and the structural feature of the at least one marker are configured to form a mechanical connection when the hygiene cover is positioned in the predefined relative position to the medical imaging device. For example, the predefined relative position of the hygiene cover to the medical imaging device may be characterized by a mechanical connection between the structural feature of the at least one marker and the structural feature of the landmark.

In providing an hygiene cover comprising at least one marker, a process of attaching the hygiene cover in the predefined relative position to the target surface and/or the body region of the patient may favorably be facilitated and/or accelerated. Furthermore, the hygiene cover may favorably support a user or operator of the medical imaging device and/or the patient in attaching the hygiene cover in the predefined position. Thus, misplacement of the hygiene cover, which may cause a contamination of the target surface and subsequent patients, may favorably be avoided.

According to an embodiment, the hygiene cover comprises:

- a material providing a cushioning effect,
- a material with a low thermal conductivity, and/or
- a material configured for inhibiting an adhesion between the hygiene cover and a skin portion of the patient.

A surface of the hygiene cover may be in direct contact with a skin portion of patient when the hygiene cover is positioned in the predefined relative position to the medical imaging device and the patient.

For example, the hygiene cover comprises or consists of one or more materials or material layers, each one providing at least one of the above-mentioned effects and/or comprising at least one of the above-mentioned properties. For example, at least a section and/or a material layer of the hygiene cover may consist of an elastic foam with low thermal conductivity. The elastic foam may also be configured for providing a cushioning effect and/or inhibiting an adhesion between the hygiene cover and the skin portion of the patient.

In a further embodiment, the hygiene cover comprises a coating and/or an outer layer configured for inhibiting an adhesion between the hygiene cover and the skin portion of the patient. For example, the hygiene cover may comprise a porous surface and/or a microfiber layer for avoiding adherence to the skin portion of the patient.

For example, the material of the hygiene cover may have any suitable thermal conductivity such as e.g. in the range of 0 to 20 W/m·K, 0 to 10 W/m·K, 0 to 5 W/m·K, etc.

In providing a hygiene cover, a comfort of the patient during an imaging examination may favorably be enhanced. Thus, a risk of a discontinuation of the imaging examination due to discomfort may favorably be decreased.

The medical imaging device for performing an imaging examination of a patient comprises a hygiene cover according to an embodiment described above. The hygiene cover is configured for reversibly attaching to a target surface of the medical imaging device. The reversible attachment is configured to maintain the predefined relative position of the hygiene cover to the medical imaging device during the imaging examination.

The medical imaging device may be embodied according to an embodiment described above. In an embodiment, the medical imaging device is a magnetic resonance device or an x-ray device.

The target surface may represent a surface of a housing of the medical imaging device. However, the target surface may also represent a surface of an imaging component and/or a support structure of the medical imaging device. For example, the target surface may relate to a surface of a local coil of magnetic resonance device. The local coil may be configured as a surface coil positioned on a surface of the body region of the patient, when the hygiene cover attached to the target surface and/or the body region in the predefined relative position to the medical imaging device.

The medical imaging device shares the advantages of the hygiene cover.

In one embodiment, the medical imaging device comprises a vacuum system configured for providing negative pressure, wherein the target surface comprises a perforation connected to the vacuum system and wherein the vacuum system is configured to hold the hygiene cover on the target surface in the predefined relative position to the medical imaging device via the negative pressure.

The vacuum system may be an integral component of the medical imaging device. However, the vacuum system may also represent a separate component. For example, the medical imaging device may comprise a (quick) connector configured for connecting the vacuum system to the medical imaging device.

The medical imaging device may comprise one or more perforations distributed in regular or irregular intervals across the target surface.

In one embodiment, the medical imaging device comprises a piping system or channels connecting the one or more perforations in the target surface to the vacuum system. The piping system or channels may be housed within the medical imaging device. It is also conceivable that the piping system or channels are at least partially embedded within the target surface.

The hygiene cover may be held in the predefined relative position to the target surface by the negative pressure at the inlets of the one or more perforations.

In providing an medical imaging device, a piping system embedded within the hygiene cover and/or further fastening elements may be omitted. Thus, a handling and/or a weight of the hygiene cover may favorably be improved.

According to a further embodiment of the medical imaging device, the target surface of the medical imaging device comprises at least one landmark. The at least one landmark is configured to provide guidance for aligning at least one marker of the hygiene cover with the at least one landmark when reversibly attaching the hygiene cover to the target surface in the predefined relative position to the medical imaging device.

As described above, the at least one landmark may comprise a structural feature and/or a visual feature.

A landmark may represent a geometric anomaly on the target surface. For example, the at least one landmark may be characterized by an edge, a recess, a raised feature, a notch, a groove, a pin, a bolt, a screw, a rail, etc. However, the at least one landmark may also represent a silhouette or outline of the hygiene cover on the target surface. The silhouette or outline of the hygiene cover may indicate a correct orientation and or position of the hygiene cover in the predefined relative position to the medical imaging device. It is also conceivable that the at least one landmark comprises a symbol, an arrow, a hand, a visual user instruction, a rectangle, a triangle, a circle, a stylized drawing of the hygiene cover, or the like.

In an embodiment, the at least one marker is in contact with the at least one landmark when the hygiene cover is positioned in the predefined relative position to the medical imaging device.

The medical imaging device comprising at least one landmark shares the advantages of the hygiene cover comprising at least one marker according to an embodiment described above.

According to a further embodiment, the medical imaging device comprises a fastening element, wherein the fastening element is configured for reversibly attaching the hygiene cover to the target surface and wherein the fastening element is configured for providing a mechanical connection between the hygiene cover and the medical imaging device.

The fastening element may be implemented according to an embodiment described above.

The medical imaging device shares the advantages of the hygiene cover including a fastening element. In providing a medical imaging device comprising a fastening element, a handling, and/or weight of the hygiene cover may favorably be improved.

BRIEF DESCRIPTION OF THE DRAWINGS

Further advantages and details of the present disclosure may be recognized from the embodiments described below as well as the drawings. The figures show.

DETAILED DESCRIPTION OF THE DISCLOSURE

Figure 1:
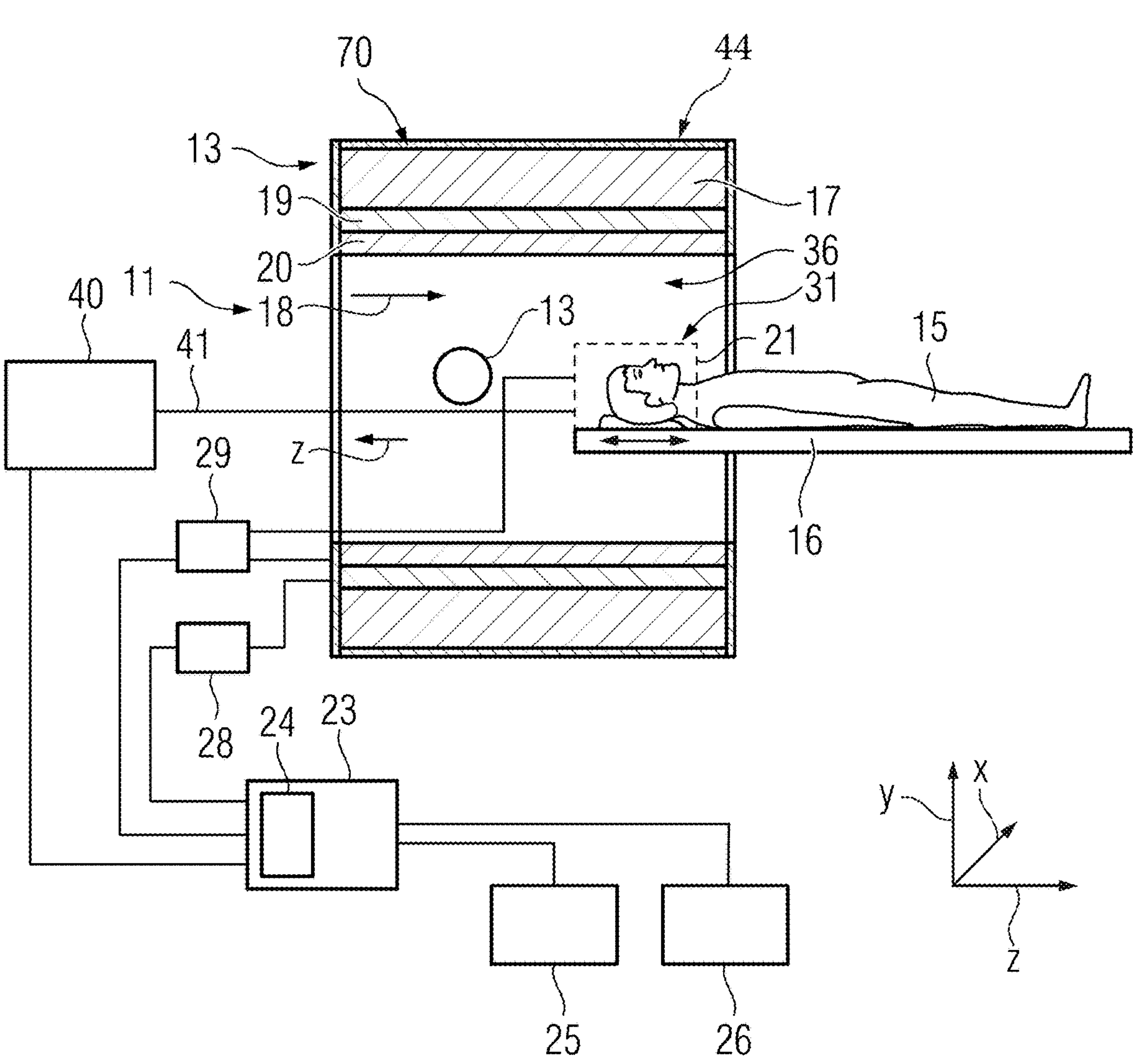
FIG. 1 illustrates an example medical imaging device, in accordance with one or more embodiments of the disclosure.

FIG. 1 illustrates an embodiment of a medical imaging device 11 according to the disclosure. In the depicted example, the medical imaging device 11 is a magnetic resonance device configured for acquiring magnetic resonance image data from an object positioned within an imaging region 36. The magnetic resonance imaging device comprises a field generation unit 44 including a cylindrical magnet 17 that provides a homogenous, static magnetic field 18 (B0 field). The static magnetic field 18 comprises an isocenter 13 and the cylindrical imaging region 36 for receiving an imaging object, such as a patient 15. The imaging region 36 may be defined by a bore configured for accommodating a patient 15 during an imaging examination, such as a magnetic resonance measurement. The imaging region 36 is surrounded or enclosed by the field generation unit 44 in a circumferential direction.

In the depicted example, the magnetic resonance imaging device 11 comprises a patient support 16 or patient table configured for transporting the patient 15 into the imaging region 36. In particular, the patient support 16 may be configured to transport a diagnostically relevant body region 31 of the patient 15 into the isocenter 13 of the magnetic resonance imaging device 11.

The magnetic resonance imaging device 11 further comprises a gradient system 19 configured for providing magnetic gradient fields used for spatial encoding of magnetic resonance signals acquired during a magnetic resonance measurement. The gradient system 19 is activated or controlled by a gradient controller 28 via an appropriate current signal. It is conceivable that the gradient system 19 comprises one or more gradient coils for generating magnetic gradient fields in different, e.g. orthogonally oriented, spatial directions.

The magnetic resonance imaging device 11 may comprise a high frequency system including a radiofrequency antenna 20 (body coil), which may be integrated into the magnetic resonance imaging device 11. The radiofrequency antenna 20 is operated via a radiofrequency controller 29 that controls the radiofrequency antenna 20 to generate a high frequency magnetic field and emit radiofrequency excitation pulses into the imaging region 36. The magnetic resonance imaging device 11 may further comprise a local coil 21, which is positioned on or in proximity to the diagnostically relevant region of the patient 15. The local coil 21 may be configured to emit radiofrequency excitation pulses into the patient 15 and/or receive magnetic resonance signals from the patient 15. It is conceivable, that the local coil 21 is controlled via the radiofrequency controller 29.

The magnetic resonance imaging device 11 may further comprise a control unit 23 configured for controlling the magnetic resonance imaging device 11. The control unit 23 may include a processing unit 24 configured for processing magnetic resonance signals and reconstructing magnetic resonance images. The processing unit 24 may also be configured to process input from a user of the magnetic resonance imaging device 11 and/or provide an output to the user. For this purpose, the processing unit 24 and/or the control unit 23 can be connected to a display unit 25 and an input unit 26 via a suitable signal connection. For a preparation of a magnetic resonance imaging measurement, preparatory information, such as imaging parameters or patient information, can be provided to the user via the display unit 25. The input unit 26 may be configured to receive information and/or imaging parameters from the user.

The magnetic resonance imaging device 11 shown in FIG. 1 comprises one or more hygiene covers 12 (not shown). For example, the patient support 16 may comprise a hygiene cover 12, such as a head cushion and/or a hole-body cover configured for covering the patient support 16. In particular, a hygiene cover 12 may be attached to a side of the local coil 21 facing in a direction of the patient 15. However, it is also conceivable that a hygiene cover 12 is attached to an inner surface of the bore or cylindrical imaging region 36.

In the depicted embodiment, the control unit 23 of the magnetic resonance device 11 is configured to control a vacuum system 40. The vacuum system 40 is connected to perforations 33 in a target surface 30 (see FIG. 5) on the local coil 21 via a piping system 41. A negative pressure provided by the vacuum system 40 is used to reversibly attach the hygiene cover 12 to the target surface 30 in a predefined relative position to the local coil 21, but also the patient 15. The control unit 23 may be configured to activate and deactivate the vacuum system 40 depending on a status of an imaging examination.

The magnetic resonance imaging device 11 may comprise further components that magnetic resonance imaging devices usually exhibit. The general operation of a magnetic resonance imaging device 11 is known to those skilled in the art, so a more detailed description is omitted.

Figure 2:
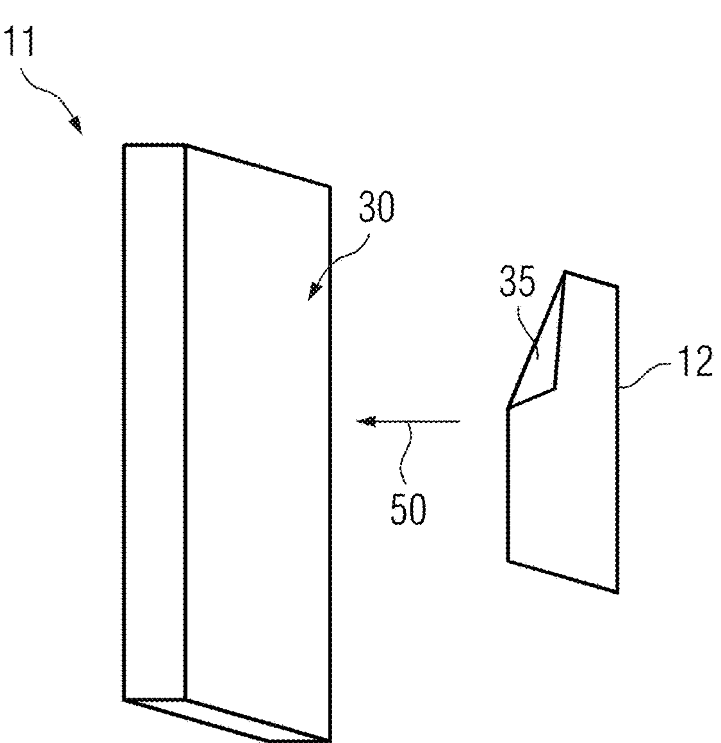
FIGS. 2-6 illustrate example schematic representations of a medical imaging device, in accordance with one or more embodiments of the disclosure.

FIG. 2 shows an embodiment of the medical imaging device 11 including a hygiene cover 12. As indicated by arrow 50, the hygiene cover 12 may reversibly attach to the target surface 30 of the medical imaging device 11. In the depicted example, a surface of the hygiene cover 12 facing towards the target surface 30 comprises an adhesive layer 35. The adhesive layer 35 is configured for providing a reversible adhesive bond between the hygiene cover 12 and the target surface 30. For example, the adhesive bond allows an operator of the medical imaging device 11 and/or a patient 15 to remove the hygiene cover 12 with manual effort and/or without leaving any residue.

As an alternative or in addition to the adhesive layer 35, the hygiene cover 12 may comprise an electrostatic charge opposite to an electrostatic charge of the target surface 30. Thus, the hygiene cover 12 may reversibly attach to the target surface via electrostatic attraction. In this case, an additional fastening element 32 or adhesive layer 35 may favorably be omitted.

In the embodiment shown in FIG. 2, the target surface 30 of the medical imaging device is substantially flat or planar. However, the target surface 30 may comprise a three-dimensional shape (i. e. see FIGS. 6 and 9). For example, the hygiene cover 12 may comprise or consist of a flexible and/or elastic material configured to be modified to conform to the shape or contour of the target surface 30.

Figure 3:
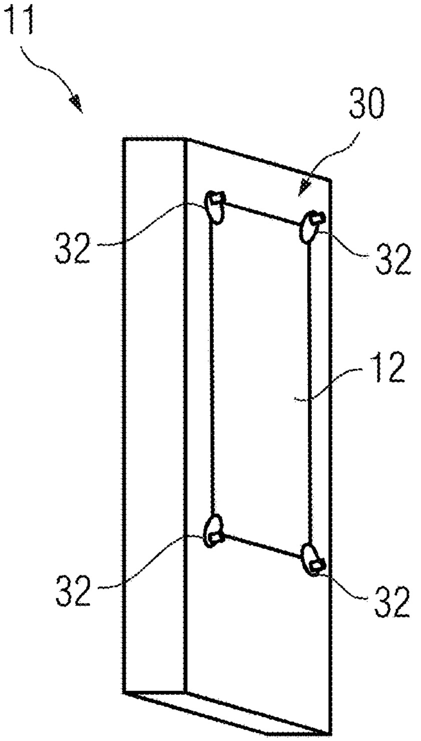

FIG. 3 shows an embodiment, wherein the medical imaging device 11 comprises fastening elements 32 configured for reversibly attaching the hygiene cover 12 to the target surface 30. In the depicted example, the fastening elements 32 comprise pins and plates rotatably mounted about the pins. A distance or gap between the target surface 30 and the plates may be slightly less than or equal to a thickness of the hygiene cover 12. Thus, the plates may provide a force-locking mechanical connection reversibly attaching the hygiene cover 12 to the target surface 30 when rotated over a section of the hygiene cover 12.

The fastening elements 32 may be implemented according to an embodiment described above.

In an alternative embodiment, the fastening elements 32 may comprise one or more magnets (not shown) configured for reversibly attaching the hygiene cover 12 to the target surface 30. The target surface 30 may comprise a magnetic or ferromagnetic material configured to magnetically interact with or attract the one or more magnets.

Figure 4:
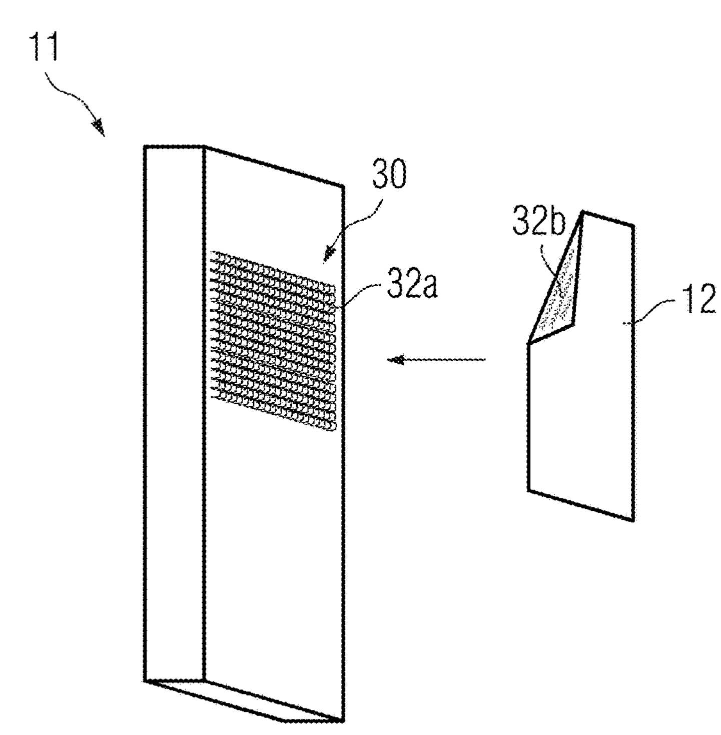

In the embodiment depicted in FIG. 4, the hygiene cover 12 is reversibly attached to the target surface 30 via fastening elements 32. A first fabric element **32*a* comprising loops is mounted on the target surface 30. A second fabric element 32*b* comprising hooks is present on a surface of the hygiene cover 12 facing in the direction of the target surface 30. When the hygiene cover 12 is positioned in the predefined position on the target surface 30, the hooks of the second fabric element 32*b* catch in the loops of the first fabric element 32*a* reversibly attaching the hygiene cover 12 to the target surface 30 of the medical imaging device 11**.

Figure 5:
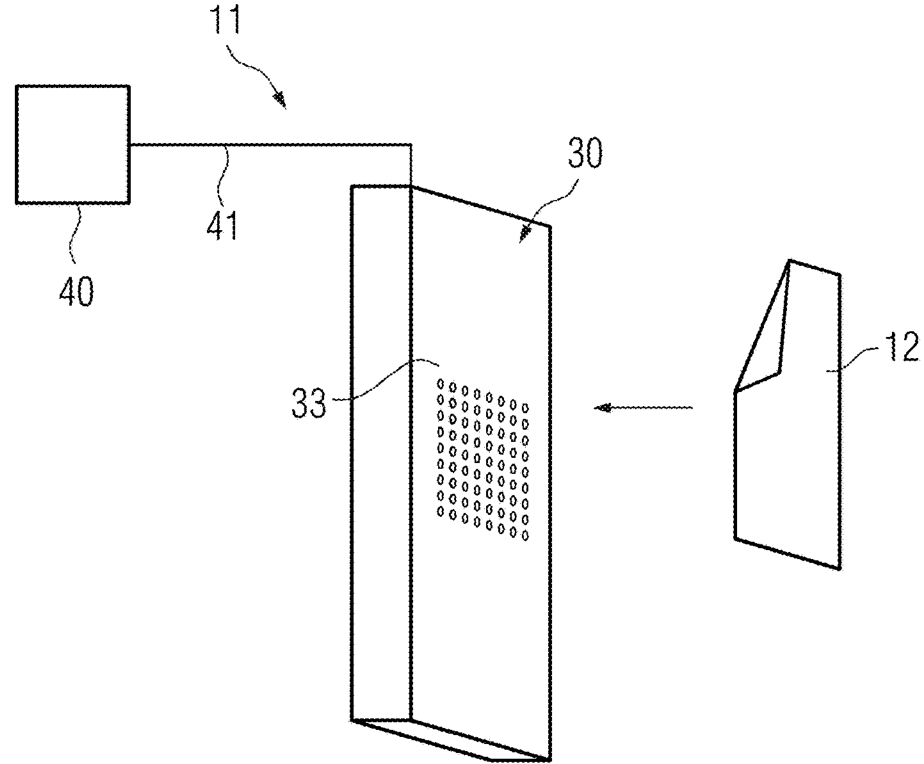

FIG. 5 depicts an embodiment of a medical imaging device 11 comprising a vacuum system 40. The vacuum system 40 is connected to perforations 33 in the target surface 30 via a piping system 41. For example, the piping system 41 may comprise or connect to channels connecting the perforations 33 to the piping system 41 and the vacuum system 40. The vacuum system 40 provides a negative pressure at inlets to the perforations 33 reversibly attaching the hygiene cover to the target surface 30.

It is also conceivable that a surface of the hygiene cover 12 comprises perforations 33 connected to the vacuum system 40.

In an embodiment, the control unit 23 and/or processing unit 24 of the medical imaging device 11 is configured to control the vacuum system 40. For example, the control unit 23 may be configured to activate the vacuum system 40 before an imaging examination is conducted. Likewise, the control unit 23 may be configured to turn off the vacuum system 40 when the imaging examination has finished and the patient 15 has left the imaging region 36. However, the control unit 23 and/or the processing unit 24 may also be configured to control a valve in the piping system 41 and/or a compressor of the vacuum system 40.

In one embodiment, the vacuum system 40 or a system connected to the piping system 41 is configured to provide a positive pressure. For example, positive pressure may be supplied to the piping system 41 to detach the hygiene cover 12 from the target surface 30. For example, the control unit 23 may be configured for controlling positive pressure and negative pressure within the piping system 41.

Figure 6:
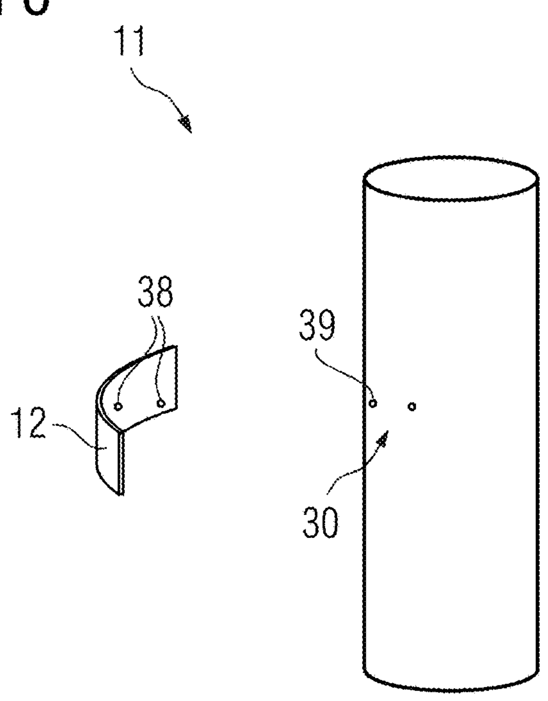

In FIG. 6, a further embodiment of the medical imaging device 11 is depicted. In the present example, the target surface 30 of the medical imaging device 11 is curved or bent. The hygiene cover 12 may comprise a flexible material allowing for the hygiene cover 12 to be deformed in correspondence with the shape of the target surface 30. However, the hygiene cover 12 may also be pre-shaped to conform to the target surface 30. In this case, the hygiene cover 12 may also comprise a rigid material.

In order to facilitate a process of positioning the hygiene cover 12 in the predefined relative position to the target surface 30, the hygiene cover 12 may comprise markers 38. For example, the markers 38 may be positioned on a side of the hygiene cover 12 facing towards the target surface 30. When positioning the hygiene cover 12 in the predefined relative position to the target surface 30, the operator or the patient 15 may align the markers 38 with corresponding landmarks 39 on the target surface 30. Thus, a process of orienting and/or positioning of the hygiene cover 12 in the predefined relative position to the target surface 30 may be facilitated.

The markers 38 and/or landmarks 39 may be visual features providing visual guidance to the operator and/or the patient 15. However, the markers 38 and/or landmarks 39 may also comprise structural features. The structural features may also function as fastening elements 32 according to an embodiment described above (i. e. see FIG. 3). For example, the first fabric element 32*a* (i. e. corresponding to a landmark 39) and the second fabric element 32*b* (i. e. corresponding to a marker 38) shown in FIG. 4 may comprise a characteristic geometry determining an orientation and/or position of the hygiene cover 12. For example, the first fabric element 32*a* and the second fabric element 32*b* may comprise an oval shape, a polygonal shape, a star shape, or the like.

However, the first fabric element 32*a* and the second fabric element 32*b* may also be subdivided into a plurality of first fabric elements 32*a* and a plurality of second fabric elements 32*b*, thus defining an orientation and/or position of the hygiene cover 12.

Figure 7:
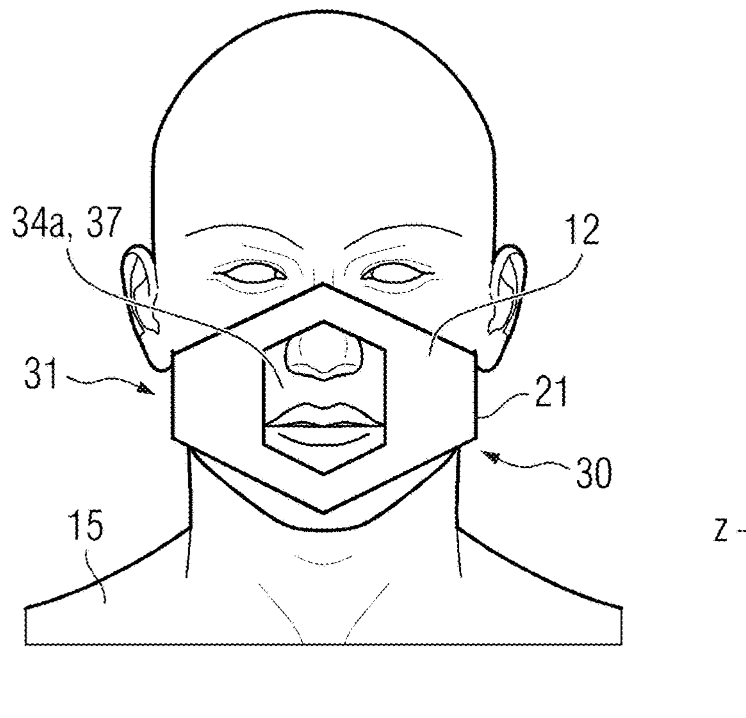
FIGS. 7-8 illustrate example hygiene covers, in accordance with one or more embodiments of the disclosure.

FIG. 7 shows a further embodiment of the hygiene cover 12. In the present example, the target surface 30 relates to a side of a local coil 21 facing towards a facial area 31 of the patient 15. The local coil 21 may be configured for acquiring magnetic resonance image data from a facial area, particularly a jaw region and/or an intraoral region of the patient 15. The local coil 21 may need to be positioned close to the facial region of the patient 15 and may bear a significant risk of contamination.

The hygiene cover 12 is reversibly attached to the target surface 30 and a skin portion of the facial area 31 of the patient 15. Thus, the hygiene cover 12 fills a gap between the target surface 30 and the facial area of the patient 15 when the hygiene cover 12 is positioned in the predefined relative position to the local coil 21 as depicted in FIG. 7.

The local coil 21 features an opening 37 to keep clear of the mouth and/or at least a part of the nose of the patient 15. The hygiene cover 12 comprises an opening or a perforation 34*a* corresponding to the opening 37 in the target surface 30 of the local coil 21. The perforation 34*a* is positioned congruently with the opening 37 in the target surface 30 when the hygiene cover 12 is positioned in the predefined relative position to the target surface 30 and the patient 15. In the depicted example, the target surface 30 and the hygiene cover 12 are located on a side of the local coil 21 facing towards the patient 15.

The hygiene cover 12 is reversibly attached to the target surface 30 according to an embodiment described above. In an embodiment, the hygiene cover 12 is attached to the target surface 30 via a hook-and-loop mechanism or a layer of adhesive 35. However, the hygiene cover 12 or the local coil 21 may also comprise perforations 33 connected to a vacuum system 40 according to an embodiment described above.

Figure 8:
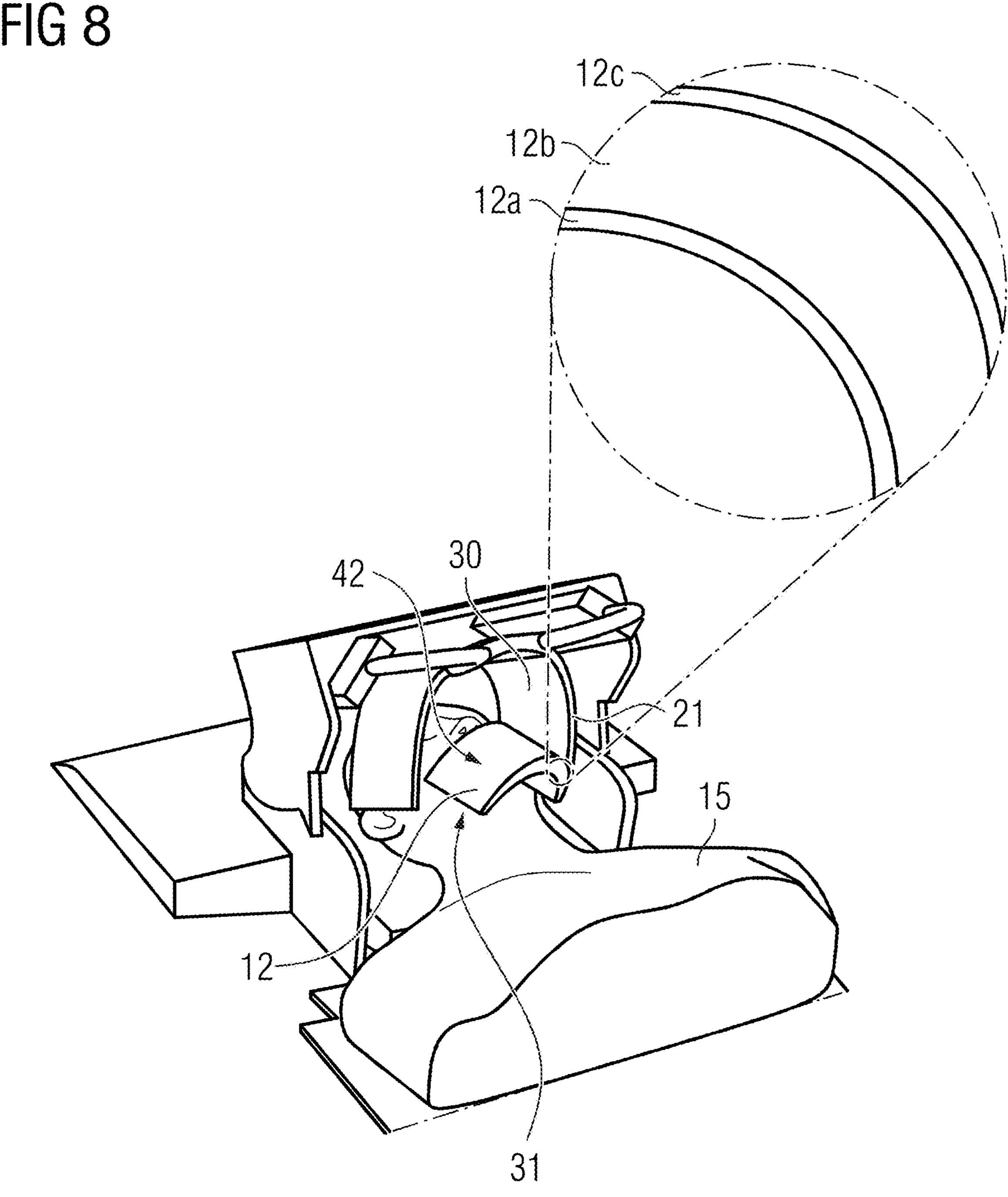

FIG. 8 shows an embodiment of the hygiene cover 12 comprising multiple materials or layers 12*a*, 12*b* and 12*c*. In the depicted embodiment, the layer 12*a* comprises microfibers for inhibiting an adhesion between the hygiene cover 12 and the skin of the patient 15. The layer 12*b* comprises an elastic polyurethane foam providing a cushioning effect. Thus, a risk of discomfort or injury of the patient 15 is reduced when the local coil 21 is moved towards the facial region of the patient 15 when conducting an imaging examination. The layer 12*c* may for example comprise a fastening element 32 according to an embodiment described above. However, the hygiene cover 12 or one or more of the layers 12*a* to 12*c* may also comprise a barrier layer (not shown) configured for preventing a transport of a substance on the skin of the patient 15 onto the target surface 30 through or via the hygiene cover 12. For example, the layer 12*c* may comprise a hydrophobic material configured for preventing water-soluble substances from diffusing through the body of the hygiene cover 12.

In the depicted embodiment, the layer 12*b* comprising an elastic foam allows for modifying the shape of the hygiene cover 12 in such a way, that the hygiene cover conforms to a shape or contour of the facial region of the patient 15, but also to a shape or contour of the target surface 30. The local coil 21 depicted in FIG. 8 is configured to be closed over the head region of the patient 15 in such a way, that the target surface is positioned close to the skin of the patient 15. For example, the hygiene cover 12 may fill the gap 42 between the target surface 30 of the local coil 21 and the facial region of the patient 15 when the local coil 21 is closed over the head of the patient 15 and the hygiene cover 12 is positioned in the predefined relative position to the target surface 30 and the patient 15. Thus, the jaw region of the patient 15 may favorably be held in place in a relative position to the medical imaging device 11.

Figure 9:
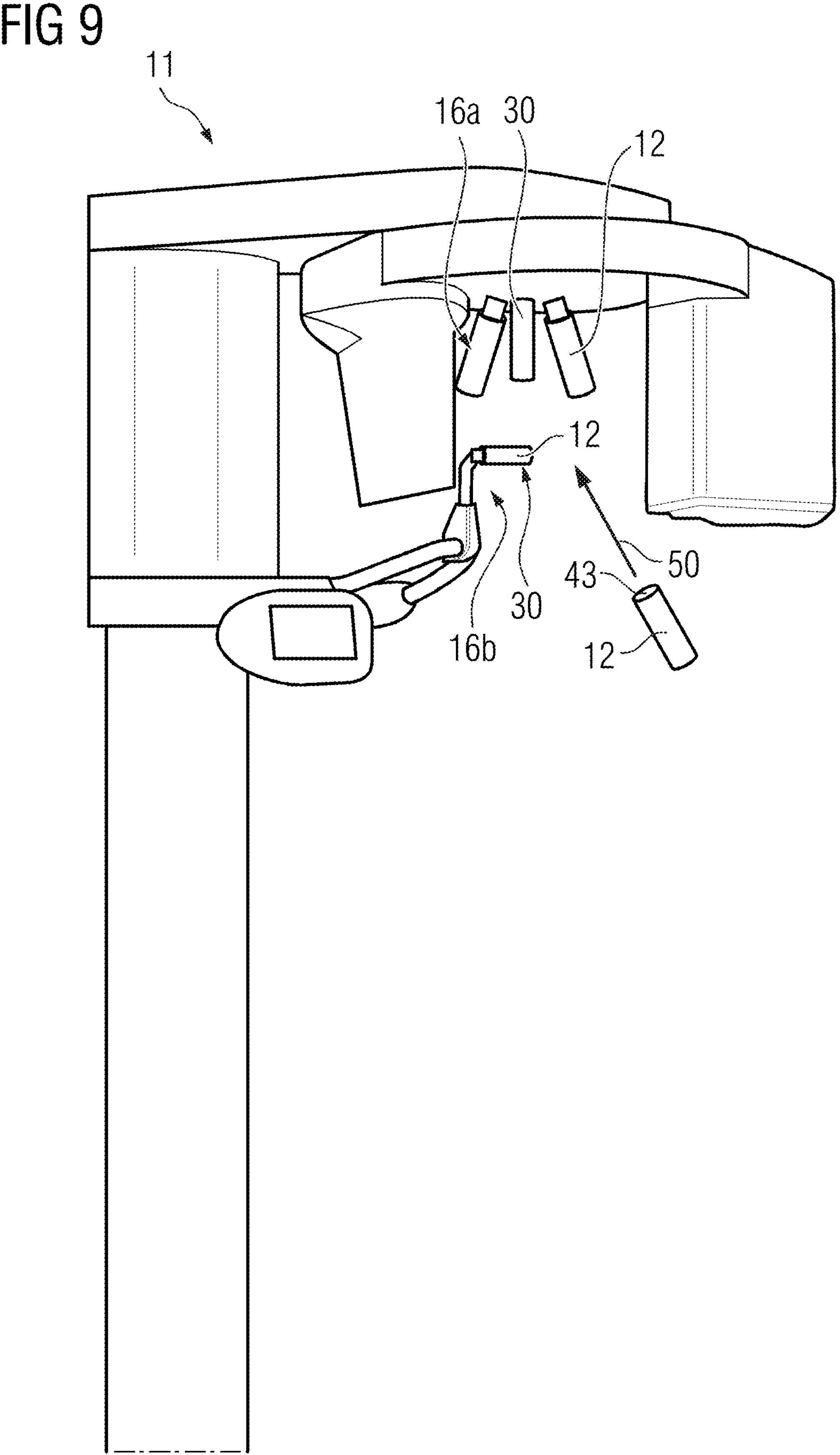
FIG. 9 illustrates another example medical imaging device, in accordance with one or more embodiments of the disclosure.

FIG. 9 shows an embodiment, wherein the medical device 11 is an x-ray device, e.g. an x-ray device for imaging teeth of a patient 15. The patient support 16 of the x-ray device 11 comprises a head support 16*a* and a chin support or jaw rest 16*b*. The head support 16*a* is configured to limit or prevent movement of the patient's head during an imaging examination. The jaw rest 16*b* may be configured to prevent movement of the lower jaw of the patient 15, but also restrict a movement of the patient's head.

In the depicted example, the hygiene covers 12 are formed as tubes or bags. The hygiene covers 12 comprise openings 43 configured for circumferentially encompassing sections of the patient supports 16*a* and 16*b*. For example, the hygiene covers 12 may be slid over sections of the patient supports 16*a* and 16*b* as indicated by arrow 50. The hygiene covers 12 may e.g. comprise an elastic material reversibly attaching the hygiene cover 12 to the support elements 16*a* and 16*b* via elastic contraction. Thus, the elastic material may represent a fastening element 32.

In one embodiment, hygiene covers 12 according to an embodiment described above may also be reversibly attached to a target surface on the emitter unit and/or the detector unit arranged at opposing sides with respect to the support elements 16*a* and 16*b*.

Figure 10:
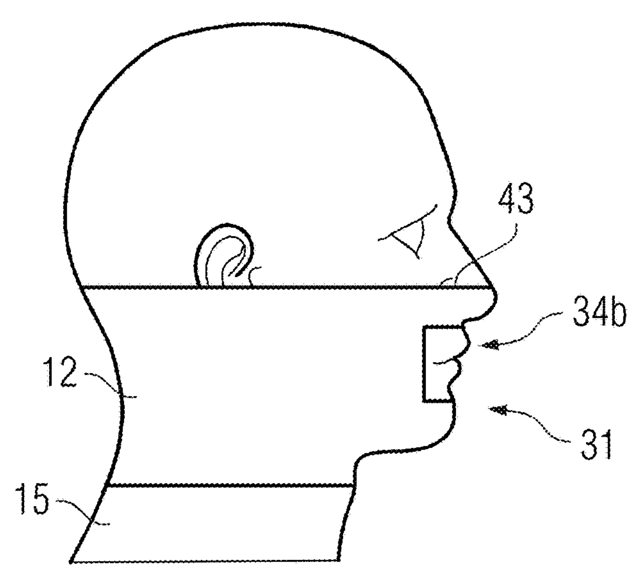
FIGS. 10-11 illustrate additional example hygiene covers, in accordance with one or more embodiments of the disclosure.

In FIG. 10 a further embodiment of the hygiene cover 12 is depicted. The hygiene cover 12 comprises a tubular shape with an opening 43 configured for circumferentially encompassing a section of a body region, particularly a head or a jaw region, of the patient 15. Furthermore, the hygiene cover 12 comprises a perforation 34*b* positioned congruently with the mouth and/or the nose of the patient 15 when the hygiene cover 12 is positioned in the predefined relative position.

In one embodiment, the perforation 34*b* in the hygiene cover 12 is positioned congruently with an opening 37 in the target surface 30 (see FIG. 7) when the hygiene cover 12 is positioned in the predefined relative position to the target surface 30 and the patient 15.

The hygiene cover 12 may comprise or consist of an elastic material which allows for stretching and facilitates a process of sliding the hygiene cover 12 over the head of the patient 15.

Figure 11:
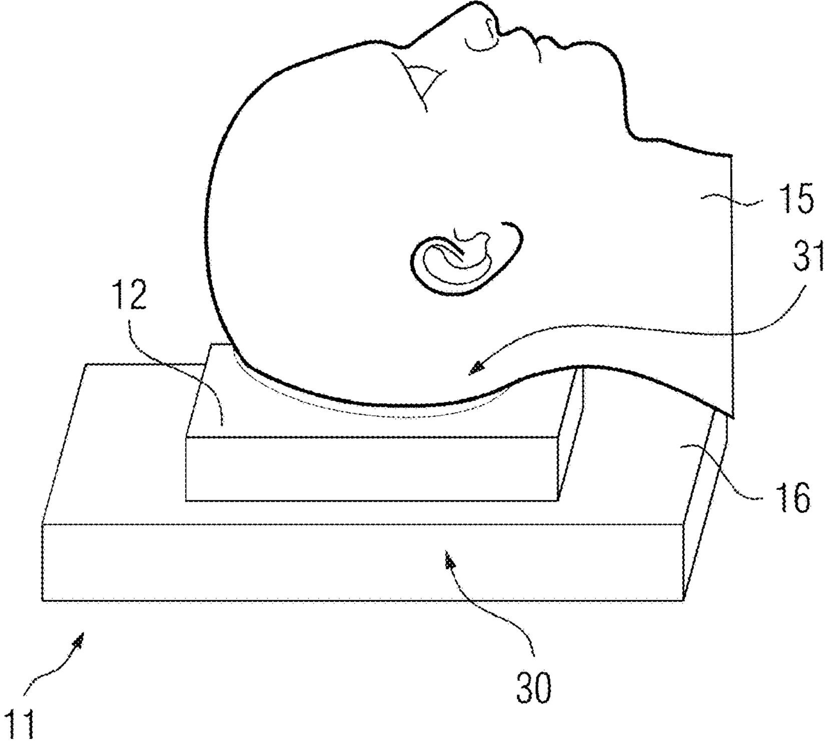

FIG. 11 shows a further embodiment of the hygiene cover 12. In the depicted example, the hygiene cover 12 is reversibly attached to a patient table 16 according to an embodiment described above. For example, the hygiene cover 12 may comprise an elastic foam configured for providing a cushioning effect. For example, the elastic foam may be made of polyurethane or polyester. In one example, the hygiene cover 12 represents a cushion configured for accommodating the head of the patient 15. In a further example, the hygiene cover 12 represents a cover or pillowcase configured for preventing a contamination of the cushion during the imaging examination.

The embodiments described above are to be recognized as examples. It is to be understood that individual embodiments may be extended by or combined with features of other embodiments if not stated otherwise.

Independent of the grammatical term usage, individuals with male, female or other gender identities are included within the term.

The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, as applicable and relevant, may alternatively be referred to herein as "circuitry," "controllers," "processors," or "processing circuitry," or alternatively as noted herein.

What is claimed is:

1. A hygiene cover configured to prevent contamination of a target surface of a medical imaging device, wherein the hygiene cover is configured to be removably attached to (i) the target surface of the medical imaging device, and (ii) a body region of a patient, to maintain a predefined relative position of the hygiene cover with respect to the medical imaging device, and wherein a section of the hygiene cover has a predetermined shape configured to fill a gap between the target surface of the medical imaging device and the body region of the patient when the hygiene cover is positioned in the predefined relative position with respect to the medical imaging device.

2. The hygiene cover according to claim 1, wherein the hygiene cover is configured to be removably attached to the target surface and the body region of the patient via a fastener, the fastener being configured to provide a mechanical connection between (i) the hygiene cover and the medical imaging device, or (ii) the hygiene cover and the patient.

3. The hygiene cover according to claim 1, further comprising:

an adhesive layer configured to provide a removable adhesive bond between the hygiene cover and the target surface of the medical imaging device, wherein the adhesive layer is configured to enable the removable adhesive bond to be activated and deactivated via a dedicated activation and deactivation process, respectively.

4. The hygiene cover according to claim 1, wherein a surface of the hygiene cover comprises a perforation connectable to a vacuum system, and wherein the hygiene cover is configured to be removably attached to the target surface of the medical imaging device via a negative pressure provided by the vacuum system.

5. The hygiene cover according to claim 1, further comprising:

a flexible section configured to enable the hygiene cover to conform to a shape of the target surface of the medical imaging device or the body region of the patient.

6. The hygiene cover according to claim 1, wherein the hygiene cover is formed as a tube comprising an opening configured to circumferentially encompass a section of the medical imaging device comprising the target surface or the body region of the patient.

7. The hygiene cover according to claim 1, further comprising:

an opening, wherein the hygiene cover is shaped to enable the opening to be positioned congruently with an opening in the target surface when the hygiene cover is positioned in the predefined relative position with respect to the medical imaging device.

8. The hygiene cover according to claim 1, further comprising:

an opening, wherein the hygiene cover is shaped to enable the opening to be positioned congruently with a facial feature of the patient when the hygiene cover is positioned in the predefined relative position with respect to the medical imaging device.

9. The hygiene cover according to claim 1, further comprising:

a barrier layer configured to prevent a transport of a substance from the patient onto the target surface of the medical imaging device via the hygiene cover.

10. The hygiene cover according to claim 1, further comprising:

a marker configured to be aligned with a landmark on the target surface of the medical imaging device when removably attaching the hygiene cover to the target surface of the medical imaging device.

11. The hygiene cover according to claim 1, wherein the hygiene cover comprises a material (i) providing a cushioning effect, (ii) having a thermal conductivity less than a predetermined threshold value, or (iii) configured to inhibit an adhesion between the hygiene cover and a skin of the patient.

12. The hygiene cover according to claim 1, wherein the target surface comprises (i) a surface of a radio-frequency coil of a magnetic resonance device, (ii) a surface of an emitter or detector of an x-ray device, (iii) a surface of a supporting structure configured to support or fix the body region of the patient in a predefined relative position to the medical imaging device, or (iv) a surface of a housing of a medical imaging device, and wherein the surface of the housing of the medical imaging device comprises a surface of a housing of a magnetic resonance device, a surface of a housing of an x-ray device, a surface of a housing of a computed tomography device, a surface of a housing of a mammography device, a surface of a housing of a positron emission tomography device, or a surface of a housing of a single-photon emission computed tomography device.

13. The hygiene cover according to claim 1, wherein the section of the hygiene cover that occupies the gap between the target surface and the body region of the patient comprises a foam padding material.

14. The hygiene cover according to claim 1, wherein the section of the hygiene cover that occupies the gap between the target surface and the body region of the patient conforms to a contour of the target surface and a contour of the body region of the patient.

15. The hygiene cover according to claim 1, wherein the target surface comprises a surface of a local coil of a magnetic resonance device that is directed towards a facial region of the patient.

16. A medical imaging device for performing an imaging examination of a patient, comprising:

a target surface comprising (i) a surface of a radio-frequency coil of a magnetic resonance device, (ii) a surface of an emitter or detector of an x-ray device, (iii) a surface of a supporting structure configured to support or fix the body region of the patient in a predefined relative position to the medical imaging device, or (iv) a surface of a housing of a medical imaging device; and a hygiene cover configured to be removably attached to (i) the target surface of the medical imaging device, and (ii) a body region of a patient, to maintain a predefined relative position of the hygiene cover with respect to the medical imaging device during the imaging examination of the patient.

17. The medical imaging device according to claim 16, further comprising:

a vacuum system configured to provide negative pressure, wherein the target surface of the medical imaging device comprises perforations connected to the vacuum system, and wherein the vacuum system is further configured to retain the hygiene cover on the target surface of the medical imaging device in the predefined relative position with respect to the medical imaging device via the negative pressure.

18. The medical imaging device according to claim 16, wherein the target surface of the medical imaging device further comprises a landmark, and wherein the landmark is configured to align with a marker of the hygiene cover when removably attaching the hygiene cover to the target surface of the medical imaging device in the predefined relative position with respect to the medical imaging device.

19. The medical imaging device according to claim 16, further comprising:

a fastener configured for removably attaching the hygiene cover to the target surface of the medical imaging device, wherein the fastener is configured to provide a mechanical connection between the hygiene cover and the medical imaging device.

20. The medical imaging device according to claim 16, wherein the surface of the housing of the medical imaging device comprises a surface of a housing of a magnetic resonance device, a surface of a housing of an x-ray device, a surface of a housing of a computed tomography device, a surface of a housing of a mammography device, a surface of a housing of a positron emission tomography device, or a surface of a housing of a single-photon emission computed tomography device.

* * * * *